United States Patent [19]

Maas

[11] Patent Number: 5,365,566

[45] Date of Patent: Nov. 15, 1994

[54] RADIATION DIAPHRAGM

[75] Inventor: Michael Maas, Uttenreuth, Germany

[73] Assignee: Siemens Aktiengesellschaft, Munich, Germany

[21] Appl. No.: 86,657

[22] Filed: Jul. 6, 1993

[30] Foreign Application Priority Data

Aug. 24, 1992 [DE] Germany .................. 4228082

[51] Int. Cl.⁵ .............................. G21K 1/04
[52] U.S. Cl. ........................ 378/150; 378/145; 378/147
[58] Field of Search ............ 378/150, 145, 147, 148, 378/149, 151, 152, 153, 156, 157, 158, 159

[56] References Cited

U.S. PATENT DOCUMENTS

| | | | |
|---|---|---|---|
| 3,649,835 | 3/1972 | Brackenbrough et al. | 378/153 X |
| 4,597,096 | 6/1986 | Larsson | 378/150 X |
| 4,715,056 | 12/1987 | Vlasbloen et al. | 378/150 X |
| 4,947,417 | 8/1990 | Hartwell. | |

FOREIGN PATENT DOCUMENTS

3500812  7/1986  Germany.

*Primary Examiner*—David P. Porta
*Attorney, Agent, or Firm*—Hill, Steadman & Simpson

[57] ABSTRACT

The invention is directed to a radiation diaphragm comprising a diaphragm lamella at which adjustment means engage, so that the diaphragm lamella is adjustable in the beam path of a radiation transmitter. Inventively, the diaphragm lamella is composed of an elastic material. The diaphragm lamella can thus be matched to the shape of an examination subject in a simple way.

12 Claims, 7 Drawing Sheets

RADIATION DIAPHRAGM

BACKGROUND OF THE INVENTION

1. Field of the Invention

The present invention is directed to a radiation diaphragm of the type having a diaphragm lamella engaged by an adjustment system, so that the lamella is adjustable in the ray beam of a radiation transmitter.

2. Description of the Prior Art

European Application 0 373 285 discloses a gating device for an x-ray diagnostics installation which includes a rigid element that is adjustable around a longitudinal axis in a plane perpendicular to the useful ray beam, and which has an arcuate edge. As a result of the variable arrangement of the arcuate edge, the useful ray beam can be individually matched to (gated onto) an arcuately shaped examination subject.

German OS 35 00 812 discloses a gating mechanism for x-radiation which includes rigid diaphragm lamellae adjustable into the ray beam, these lamellae lying against one another parallel to both sides of a slot, and being individually adjustable in the longitudinal direction by an adjustment system dependent on the size of a subject.

In angiographic examinations, for example of the legs of a patient, x-radiation is incident on regions of an image intensifier, used as the radiation receiver, which are not shadowed by the legs directly. Those regions may comprise a relatively large-area. The excessively high radiation intensity in these regions leads to a degradation of the image quality due to reduction of contrast and glare; moreover, the stray radiation is unnecessarily increased.

In order to counter these negative effects, diaphragms, for example of sheet lead, are employed, which are laterally moved into the beam path so that they are matched as well as possible to the contours of the examination subject. This gating is suitable in order to blank the ray beam at the sides of the legs. Strip-shaped diaphragms having a fixed shape that are arranged in the region between the legs are employed for blanking radiation that is incident on the image intensifier between the legs. It is also possible to provide plastically deformable and absorbent volumes, for example sacks of rice flour, in this region. This technique, however, is difficult to manipulate and increases the stray radiation.

SUMMARY OF THE INVENTION

It is an object of the present invention to implement a radiation diaphragm of the type having a lamella adjustable by an adjustment system, such that the radiation that is incident directly on the radiation receiver, and is thus unattenuated, is blanked as well as possible.

This object is achieved in accordance with the principles of the present invention in a radiation diaphragm wherein the diaphragm lamella is flexible, preferably composed of elastic material, and wherein means are provided for flexing the diaphragm lamella so that radiation absorption can be well-matched to examination subjects that differ in shape.

Preferably, elements of the adjustment system engage the diaphragm lamella such that the diaphragm lamella is adjustable around an axis aligned perpendicularly relative to the central ray of the ray beam, since the effective width of the diaphragm lamella can thus be set in a continuum within a broad range.

For use within an examination subject not having any straight limiting lines but instead having only contours curved, the adjustment system preferably engages end faces of the diaphragm lamella lying opposite one another, and the end faces are adjustable along the aforementioned axis and toward one another. The diaphragm lamella can thus be well-matched to arcuate examination subjects.

An improved adaptability of the diaphragm lamella to different examination subjects is achieved in an embodiment wherein the adjustment system includes first and second holders for the diaphragm lamella which are adjustable independently of one another. The adjustment possibilities of the diaphragm lamella are thus enhanced.

Preferably the diaphragm lamella is composed of rubber containing lead oxide since it is thus extremely flexible and has a high radiation absorption.

The diaphragm lamella may be composed of a plurality of sub-lamellae, or a plurality of elastic diaphragm lamellae may be provided that are adjustable relative to one another, thereby enhancing the adaptability of the diaphragm lamella to examination subjects having different shapes.

DESCRIPTION OF THE PREFERRED EMBODIMENTS

Figure 1:
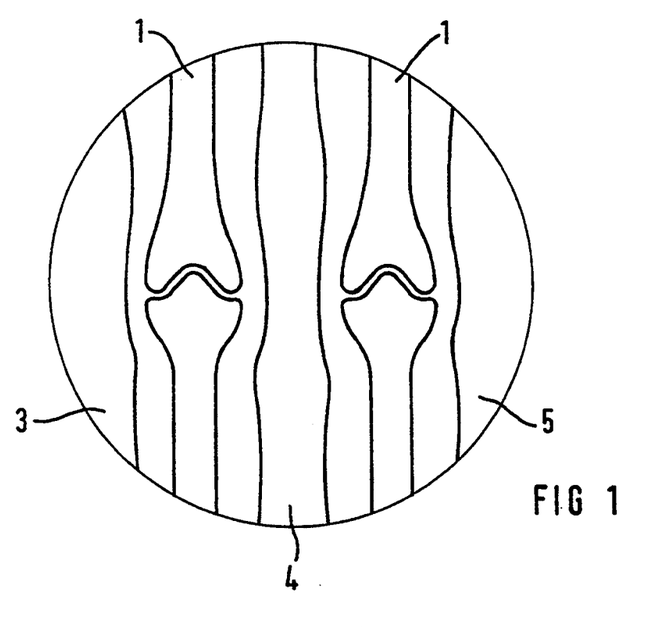
FIG. 1 shows a transillumination x-ray image of an examination subject on a monitor.
Figure 2:
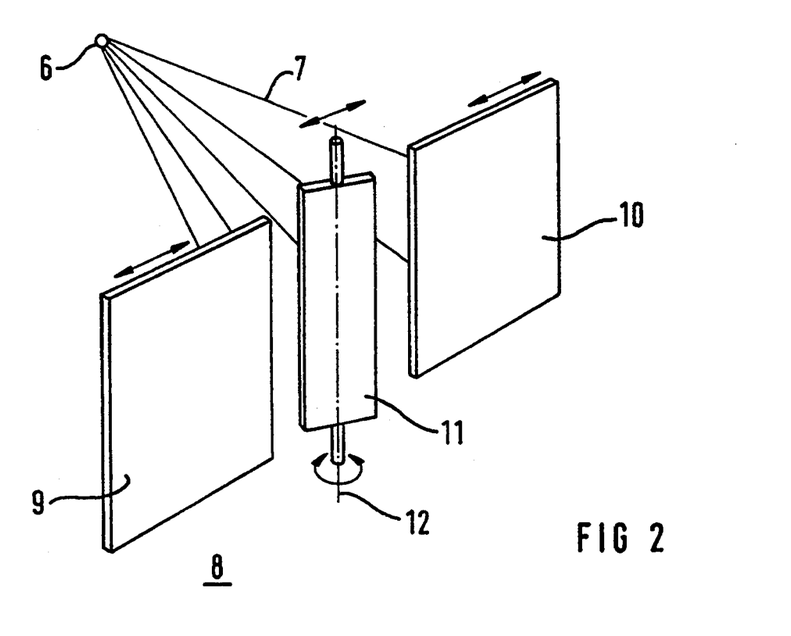
FIG. 2 shows a radiation diaphragm constructed in accordance with the principles of the present invention.

FIG. 1 shows a transillumination image of an examination subject, for example legs 1. Regions in which the radiation of a radiation transmitter 6 (shown in FIG. 2) would be incident directly on a radiation receiver (not shown) i.e., unattenuated regions, are identified with reference numerals 3, 4 and 5. Since the radiation directly incident on these regions 3, 4 and 5 results in an undesirable over-drive of the radiation receiver, such as an image intensifier, a radiation diaphragm 8 constructed in accordance with the invention is arranged in the beam path of the ray beam 7 of the radiation transmitter 6 between the radiation transmitter 6 and the examination subject, as shown in FIG. 2.

This radiation diaphragm 8 includes first and second diaphragm lamellae 9 and 10 that are laterally adjustable into the ray beam 7 for occluding the first and third regions 3 and 5. A third diaphragm lamella 11 is inventively composed of elastic material and is arranged between the first and second diaphragm lamellae 9 and 10. This third diaphragm lamella 11 serves the purpose of occluding the radiation that would be incident in the second region 4. In order to be able to vary the effective width of the third diaphragm lamella 11, it is adjustable around an axis 12 aligned perpendicularly relative to the central ray of the ray beam 7. Preferably, the third diaphragm lamella 11 is also adjustable in the plane perpendicular to the central ray of the ray beam 7, so that its alignment can be matched better to the examination subject.

Figure 3:
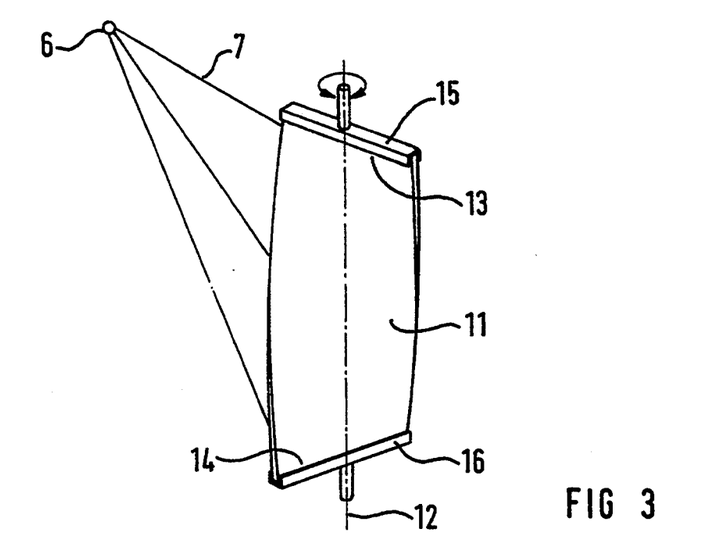
FIGS. 3 through 9 show different embodiments of the diaphragm lamella of the radiation diaphragm according to FIG. 2.
Figure 4:
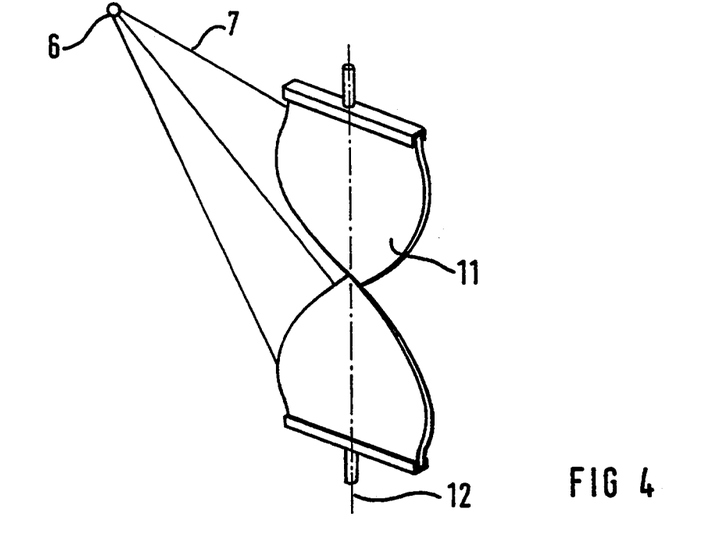
Figure 5:
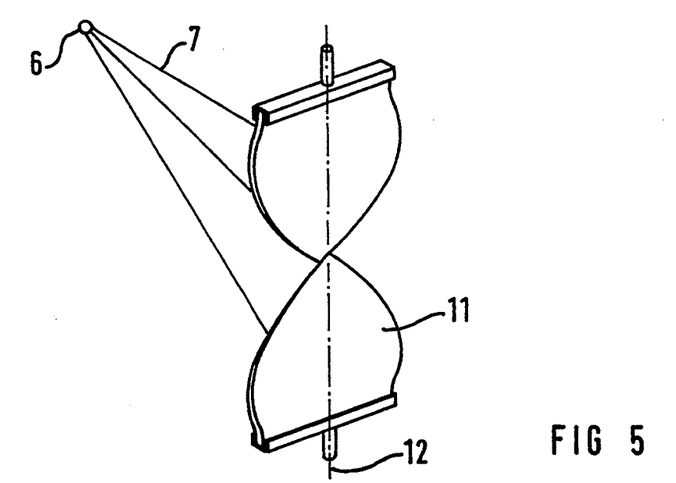

In the embodiment of FIGS. 3, 4 and 5 adjustment means in the form of holders 15 and 16 are attached at opposite end faces 13 and 14 of the third diaphragm lamella 11, the diaphragm lamella 11 being adjustable around the axis 12 by means of holders 15 and 16, One holder 16 can be stationary while the other holder 15 is adjustable around the axis 12. Preferably, however, both holders 15 and 16 are adjustable around the axis 12 in the same direction or in opposite directions.

FIGS. 4 and 5 show exemplary shapes the third diaphragm lamella can assume when the holders 15 and 16 are adjusted around the axis 12.

Figure 6:
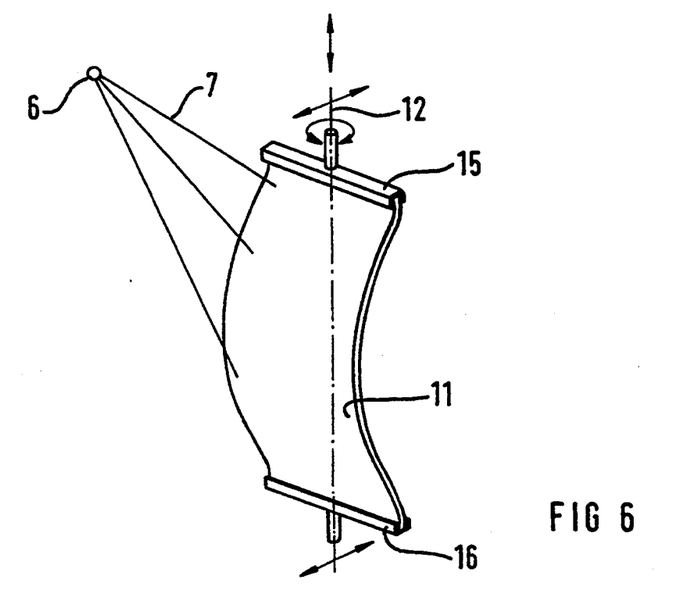

For examinations wherein it is desired that the third diaphragm lamella 11 arcuately gate a region, the holders 15 and 16 are adjustable along the axis 12 and toward one another, as shown in FIG. 6.

Figure 7:
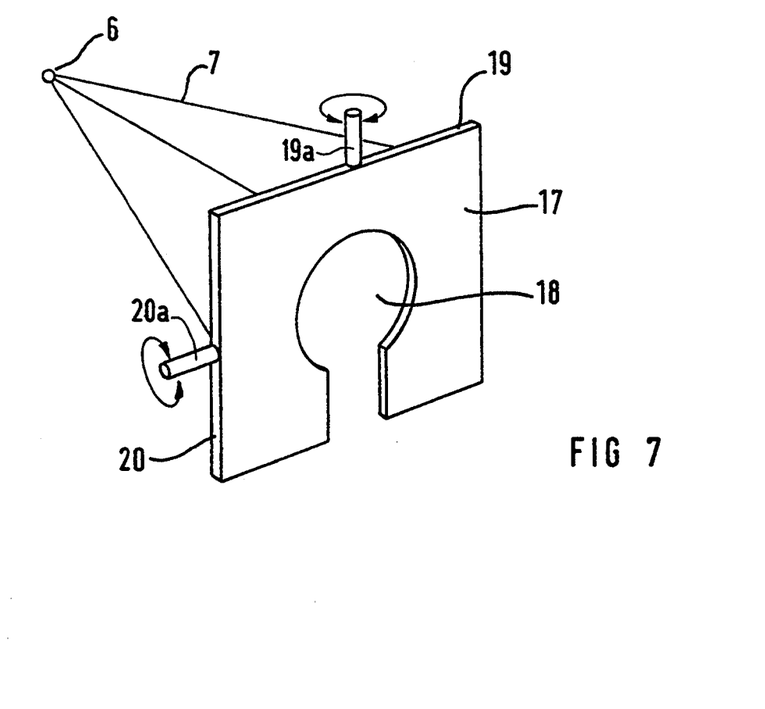

The radiation diaphragm of the invention can include a diaphragm lamella 17 shown in FIG. 7. The lamella 17 may be used in place of the lamella 11 and is likewise elastic, and has a mushroom-shaped cut-out, so that the ray beam 7 can be gated to correspond to the head of an examination subject. In order to enable the gating of the ray beam 7 corresponding to different head shapes, adjustment elements 19a and 20a of an adjustment system engage the fourth diaphragm lamella 17 at respective sides 19 and 20, aligned perpendicularly relative to one another.

Figure 8:
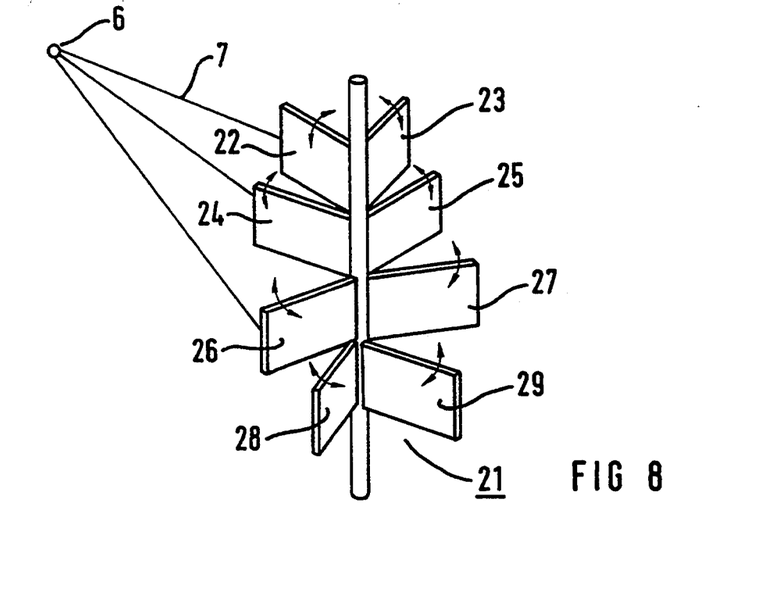

As shown in FIG. 8, the radiation diaphragm of the invention can include diaphragm lamella 21 formed by a plurality of sub-lamellae 22 through 29, mounted on an adjustment element 37 so that the alignment of the sub-lamellae 22 through 29 in the ray beam 7 is individually adjustable.

Figure 9:
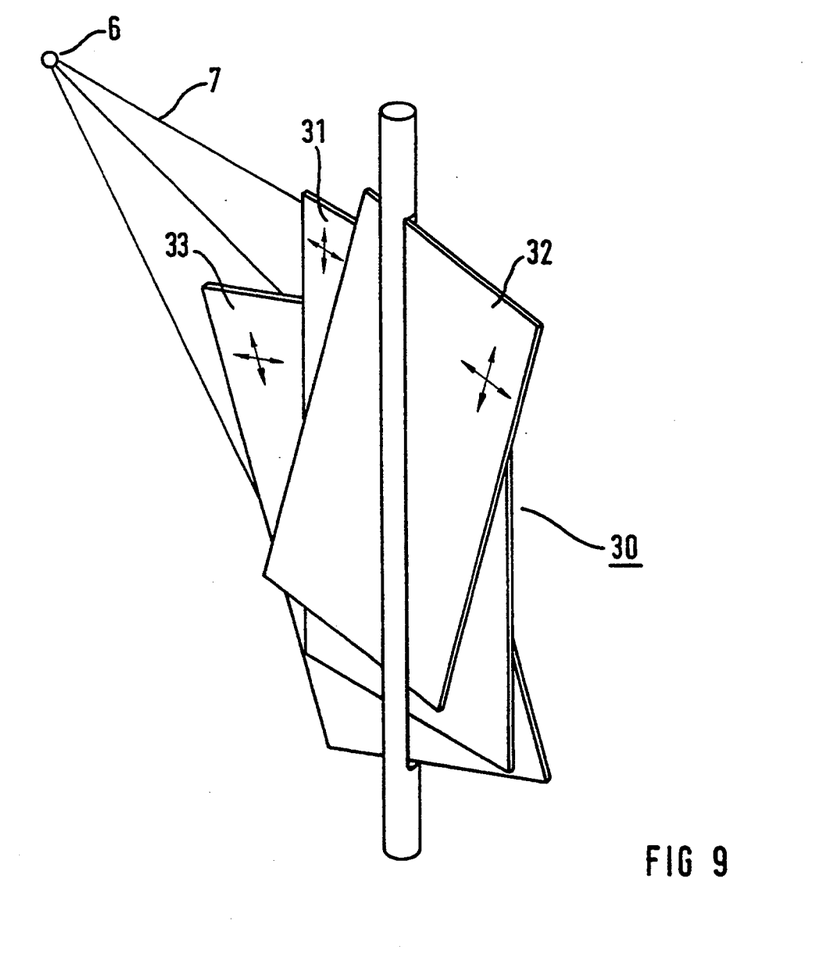

FIG. 9 shows a diaphragm lamella 30 of the radiation diaphragm of the invention, formed by individual lamellae 31 through 33 that are aligned parallel to one another and are mounted on an adjustment element 38 so as to be adjustable relative to one another. It is thus possible to give the diaphragm lamella 30 different shapes.

The adjustment system for the diaphragm lamellae 11, 17, 21 and 30 can have an electromechanical drive, for example an electric motor that engages the diaphragm lamellae 11, 17, 21 or 30 via a belt or a lever articulation guided in bearings for the adjustment thereof.

The diaphragm lamellae 11, 17, 21 and 30 are preferably composed of an elastic material, for example rubber containing lead oxide, however, they can alternatively be composed of metal sheets arranged in a scale-like pattern.

In accordance with the invention, the first and second diaphragm lamella 9 and 10 can likewise be flexible, such as composed of an elastic material, and can be rotatably and/or tiltably seated in the beam path by a correspondingly executed holder.

The radiation diaphragm of the invention is preferably arranged optimally close to the radiation source 7, since it thus has a small, economical structure. The radiation diaphragm, however, must have dimensions such that the diaphragm lamellae have an adequate thickness for radiation absorption. The area of the diaphragm projection can be varied by varying the spacing relative to the focus of the radiation transmitter 6.

The alignment of the diaphragm lamellae in the ray beam 7 can ensue in various ways. Due to the versatility of the elastic diaphragm lamellae, a user-friendly, automatic diaphragm alignment based on the content of a video system following the image intensifier can be implemented in addition to manual setting with visible auxiliary radiation. For automatic alignment of the diaphragm lamellae, only a brief-duration drive of the radiation transmitter 6 with low energy is then required, so that the radiation stress on the examination subject is low.

In accordance with the invention, the diaphragm lamella of the radiation diaphragm can be executed as an elastic filter lamella which, for example, can assume the shapes shown in FIGS. 10 through 13. The filter lamella 33 is composed of an elastic plate engaged by holders 34 and 35 at at least two sides lying opposite one another for the alignment in the ray beam 7 of the radiation transmitter 6. The holders 34 and 35 are held in the adjustment system such that the desired alignment of the filter lamella 33 can be effected.

Figure 10:
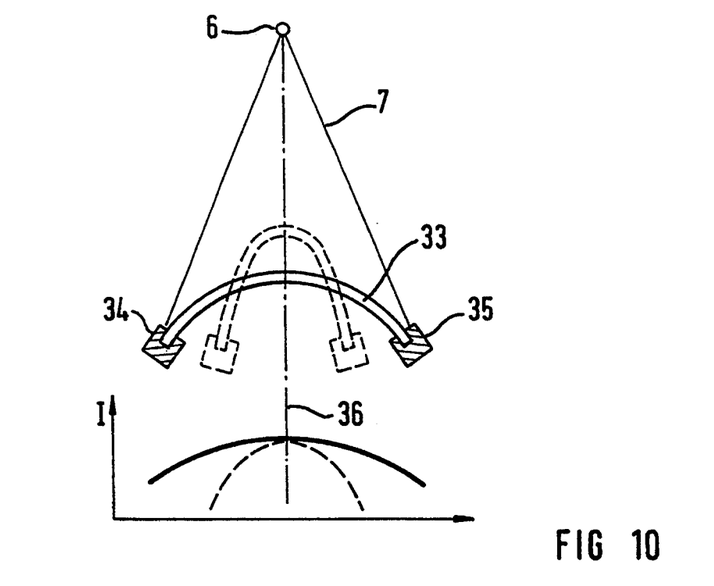
FIGS. 10 through 13 respectively show embodiments of the diaphragm lamella of the radiation diaphragm of FIG. 2, in the form of a filter.

An arcuate alignment of the filter lamella 33 is achieved as shown in FIG. 10, by adjusting the holders 34 and 35 in the direction to the central ray 36 of the ray beam 7 and/or obliquely relative thereto.

Figure 11:
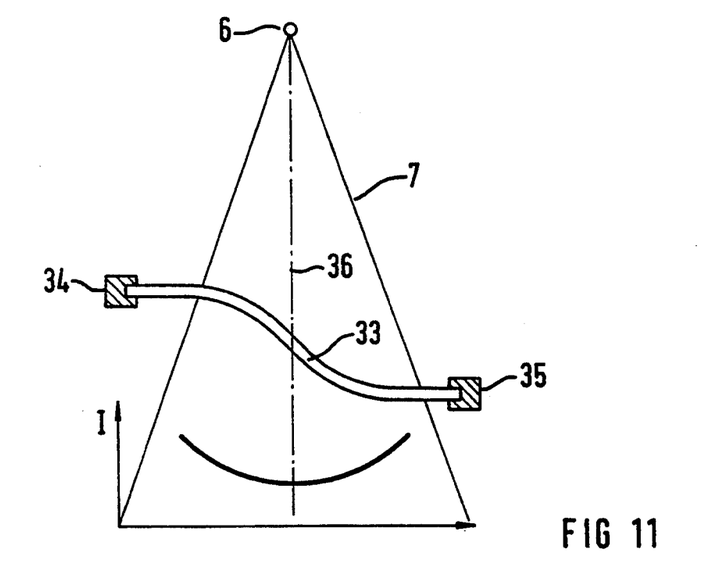

The alignment of the filter lamella 33 shown in FIG. 11 is achieved by adjusting the holders 34 and 35 in different planes perpendicularly aligned relative to the central ray 36, and in the direction to the central ray 36.

Figure 12:
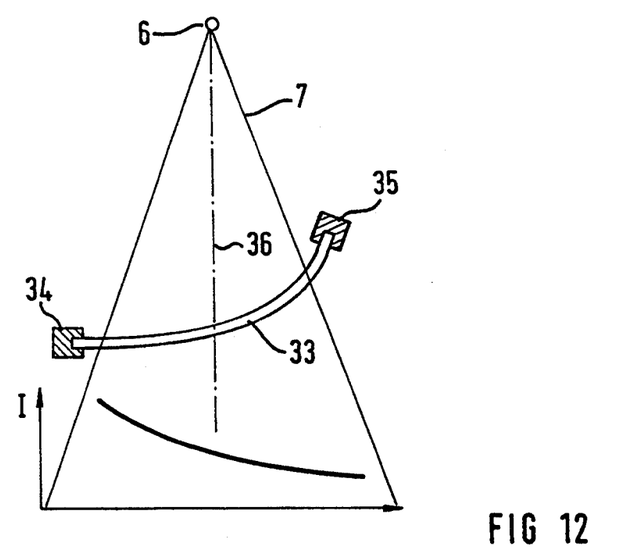

An alignment of the filter lamella 33 according to FIG. 12 is achieved by maintaining one holder, for example, the holder 34, stationary, and adjusting the holder 35 in a plane differing from the plane of the holder 34, and which is obliquely aligned relative to the central ray 36.

Figure 13:
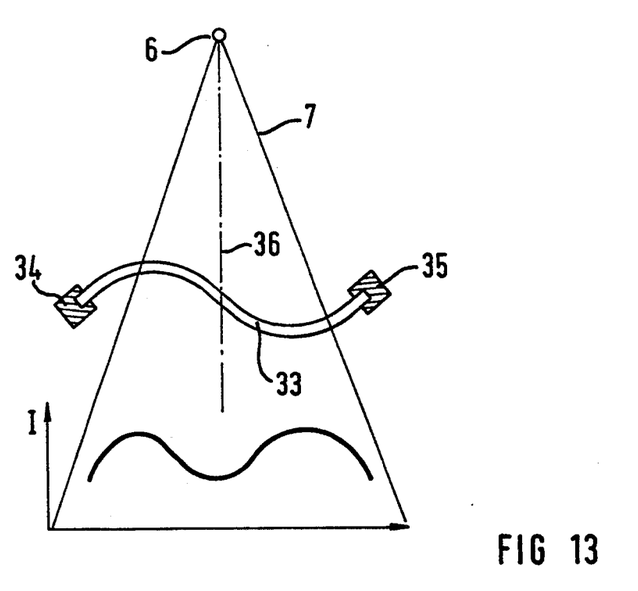

In the alignment of the filter lamella 33 shown in FIG. 13, the holders 34 and 35 are arranged in the same plane but are obliquely aligned relative to the central ray 36.

FIGS. 10 through 13 also show a diagram in which the radiation intensity I following the filter lamella is indicated.

Holders of the adjustment system can likewise be provided at further sides of the filter lamella 33 lying opposite one another Although modifications and changes may be suggested by those skilled in the art, it is the intention of the inventor to embody within the patent warranted hereon all changes and modifications as reasonably and properly come within the scope of his contribution to the art.

I claim as my invention:

1. A radiation diaphragm comprising:
   a diaphragm lamella consisting of flexible material; and
   adjustment means, engaging said diaphragm lamella, for adjusting the orientation of said diaphragm lamella by flexing said diaphragm lamella for setting a radiation absorption shape selectively matchable to different examination subjects.

2. A radiation diaphragm as claimed in claim 1 wherein said diaphragm lamella is composed of an elastic material.

3. A radiation diaphragm as claimed in claim 1 for use with an x-ray beam having a central ray, and wherein said diaphragm lamella has an axis disposed perpendicularly relative to said central ray, and wherein said adjustment means comprises means for engaging said diaphragm lamella for adjusting said diaphragm lamella around said axis.

4. A radiation diaphragm as claimed in claim 1 for use with an x-ray beam having a central ray, and wherein said diaphragm lamella has opposite ends with an axis extending between said opposite ends disposed perpendicularly relative to said central ray, and wherein said adjustment means comprises means for engaging said diaphragm lamella at said opposite ends for adjusting said opposite ends toward each other along said axis.

5. A radiation diaphragm as claimed in claim 1 wherein said diaphragm lamella has sides aligned perpendicularly relative to each other, and wherein said adjustment means comprises means for engaging said sides of said diaphragm lamella.

6. A radiation diaphragm as claimed in claim 1 wherein said adjustment means comprises a first holder engaging said diaphragm lamella and a second holder engaging said diaphragm lamella, and means for independently adjusting said first and second holders.

7. A radiation diaphragm as claimed in claim 1 wherein said diaphragm lamella is composed of rubber containing lead oxide.

8. A radiation diaphragm as claimed in claim 1 wherein said diaphragm lamella consists of a plurality of individual sub-lamellae.

9. A radiation diaphragm as claimed in claim 8 wherein said adjustment means includes means for adjusting said individual sub-lamellae relative to each other.

10. A radiation diaphragm as claimed in claim 1 wherein said diaphragm lamella is oriented by said adjustment means for use as a filter lamella.

11. A radiation diaphragm as claimed in claim 1 for use with an x-ray beam having a central ray, and wherein said diaphragm lamellae has a first axis disposed perpendicularly relative to said central ray and a second axis disposed perpendicularly relative to said central ray, said first and second axes being disposed substantially perpendicularly relative to each other, and wherein said adjustment means comprises means for engaging said diaphragm lameilae for flexing said diaphragm lamellae around each of said first and second axes.

12. A radiation diaphragm comprising a plurality of individual diaphragm lamellae that are initially aligned parallel to one another, at least one of said lamellae consisting of flexible material; and adjustment means, engaging each of said diaphragm lamellae for orienting each of said diaphragm lamellae, including flexing said at least one lamella, for setting a radiation absorption shape selectively matchable to different examination subjects.

* * * * *